United States Patent [19]

Nelson et al.

[11] 3,979,430

[45] Sept. 7, 1976

[54] SOLVOLYTIC PROCESS FOR THE PREPARATION OF 2-(5H-DIBENZO[a,d] CYCLOHEPTEN-5-ON-2-YL)ACETIC, PROPIONIC AND BUTYRIC ACIDS

[75] Inventors: Peter H. Nelson; Karl G. Untch, both of Los Altos; James P. Dunn, Palo Alto, all of Calif.

[73] Assignee: Syntex (U.S.A.) Inc., Palo Alto, Calif.

[22] Filed: Sept. 8, 1975

[21] Appl. No.: 611,057

[52] U.S. Cl. .................. 260/465 K; 260/256; 260/338; 260/340.7; 260/340.9; 260/438.1; 260/469; 260/501.1; 260/501.11; 260/515 R; 260/558 R; 424/317
[51] Int. Cl.² ....................................... C07C 121/66
[58] Field of Search ............................ 260/465 K

[56] References Cited

UNITED STATES PATENTS

| 3,270,067 | 8/1966 | Wendler et al. | 260/465 K |
|---|---|---|---|
| 3,317,582 | 5/1967 | Tishler | 260/465 K |
| 3,580,943 | 5/1971 | Trepanier | 260/465 K X |
| 3,649,692 | 3/1972 | Humber | 260/465 K X |
| 3,845,093 | 10/1974 | Rey-Bellet et al. | 260/465 K X |

*Primary Examiner*—Joseph Paul Brust
*Attorney, Agent, or Firm*—Alan M. Krubiner; William B. Walker

[57] ABSTRACT

2-(5H-dibenzo[a,d]cyclohepten-5-on-2-yl) acetic, propionic and butyric acids, and esters and salts thereof, are prepared by solvolysis of nitrile or amide intermediates, or of ketal-protected nitrile, amide, acid, ester or salt intermediates.

3 Claims, No Drawings

SOLVOLYTIC PROCESS FOR THE PREPARATION OF 2-(5H-DIBENZO[A,D] CYCLOHEPTEN-5-ON-2-YL)ACETIC, PROPIONIC AND BUTYRIC ACIDS

DETAILED DESCRIPTION OF THE INVENTION

The present invention is concerned with a process for preparation of 2-(5H-dibenzo[a,d]cyclohepten-5-on-2-yl) acetic, propionic and butyric acids, and esters and salts thereof. More specifically, the present invention concerns processes for the preparation of compounds of the formula

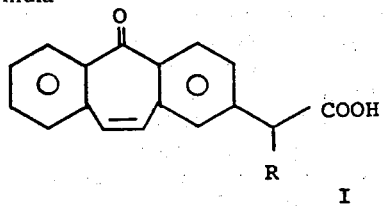

I wherein R is hydrogen, methyl or ethyl; and esters and salts thereof, from the corresponding ketonitrile or ketoamide intermediates, or from the corresponding ketal-protected nitriles, amides, acids, esters and salts.

The compounds of Formula I exhibit anti-inflammatory, analgesic and anti-pyretic activity. Accordingly, compounds of Formula I and compositions containing same are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the compounds of Formula I are useful for the relief of these conditions as well as the inflammation.

The compounds of Formula I are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus.

As used herein, esters of the carboxylic acids of Formula I or intermediates therefor refer to those esters formed from straight or branched chain alkanols having from 1 to 20 carbon atoms, such as for example, the methyl, ethyl, n-propyl, isopropyl, n-butyl, t-butyl, n-amyl, n-hexyl, octyl, decyl, dodecyl, hexadecyl and octadecyl esters; as well as the benzyl esters. A preferred subclass of esters of Formula I are those formed from pharmaceutically acceptable non-toxic alcohols.

Salts of the carboxylic acids of Formula I or intermediates therefor refer to those salts prepared from inorganic and organic bases. Salts derived from inorganic bases include the alkali metal salts such as sodium, potassium and lithium; the alkaline earth salts such as calcium and magnesium; as well as the ammonium and copper salts. Those salts derived from organic bases include the ethanolamine, diethylamine, tris(hydroxymethyl)aminomethane, choline, caffeine, and lysine salts. A preferred subclass of salts of Formula I are those formed from pharmaceutically acceptable non-toxic bases.

The term conventional ketal protecting group refers to those ketal groups conventionally used in the art to protect a reactive ketone function, which groups are readily removable by acid hydrolysis. Classes of conventional ketal protecting groups contemplated by the above are dialkyl ketals (alkyl groups of from 1 to 6 carbon atoms) such as for example, dimethyl or diethyl ketals; alkylene ketals (alkylene of 2 to 4 carbon atoms optionally substituted with lower alkyl groups of from 1 to 4 carbon atoms) such as for example, the ethylene, 1,3-propylene, 2,2-dimethyl-1,3-propylene, 1,4-butylene and 2,3-butylene ketals; and dibenzyl ketals.

The process of the present invention may be summarized in the reaction schemes presented below:

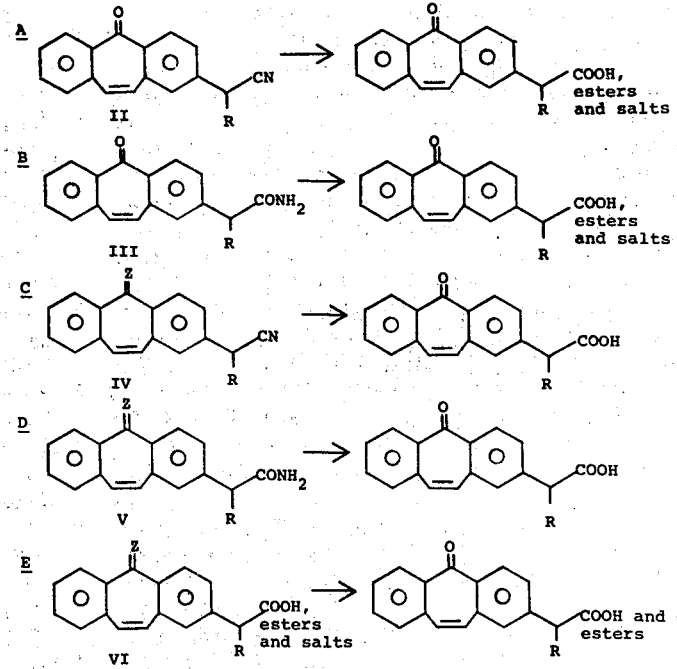

wherein R is as defined above and Z is a conventional ketal-protecting group.

In reaction scheme A is depicted the solvolysis of a keto nitrile (II) to the corresponding keto acid, ester or salt. The reaction is carried out by methods well known in the synthetic organic chemistry art under acidic or basic conditions. Reaction under basic conditions will afford, initially, the salt of the corresponding acid which may be readily converted to the free acid upon workup. Reaction under acid conditions, will afford either the free acid, or ester thereof, depending upon the solvent used, i.e., whether the reaction is conducted in an aqueous or in an alcoholic medium.

Base catalyzed hydrolysis of the nitrile to the acid, or salt thereof, may be accomplished by the use of a strong base such as, for example, an alkali metal hydroxide, e.g., sodium hydroxide or potassium hydroxide, at a temperature between about 0° and 100°C., in an aqueous solvent medium which may additionally contain water miscible organic solvents such as methanol.

Acid catalyzed hydrolysis may be carried out in the presence of a strong acid such as a mineral acid, e.g., hydrochloric acid, sulfuric acid, and the like; or a sulfonic acid such as for example p-toluenesulfonic acid, and the like, at a temperature between about 0° and 140°C., in an aqueous or alcoholic solvent medium. An aqueous solvent medium may additionally contain water miscible organic solvents such as, for example, acetic acid, to improve the solubility of the reactants.

In reaction scheme B there is depicted the conversion of a keto amide (III) to a keto acid, ester or salt. This reaction may also be carried out under acidic or basic conditions utilizing reaction conditions and reagents essentially the same as those described above for reaction scheme A.

Reaction scheme C depicts the conversion of a ketal nitrile (IV) to a keto acid. This reaction is carried out under acidic conditions essentially as described above for reaction scheme A, in an aqueous solvent medium.

Similarly, the reaction depicted in reaction scheme D, the conversion of a ketal amide (V) to a keto acid may be conducted under acidic conditions essentially the same as those used for reaction scheme C.

Reaction scheme E depicts the conversion of a ketal acid, ester or salt to the corresponding keto acid or ester by acid catalyzed solvolysis. Depending upon the nature of the conditions and reagents chosen, a starting ester may be either retained in the final product or hydrolyzed to the free acid. The removal of the ketal group may be accomplished by treating with a dilute strong acid such as a mineral acid, e.g., 1 N hydrochloric acid, or a sulfonic acid, e.g. p-toluenesulfonic acid, in, for example, an aqueous solvent medium which may additionally contain a water miscible organic solvent such as acetone or methanol, at a temperature of between about 0° and 100°C. If hydrolysis of an ester to the free acid is additionally desired, it is preferred to conduct the reaction in an aqueous medium preferably using a more highly concentrated strong acid, e.g., 5 N hydrochloric acid, at a temperature between about 25 and 100°C.

In all of the above reactions (schemes A–E) the starting materials and reagents may be contacted in any convenient manner and maintained at a temperature and for a period of time sufficient to complete the desired reaction. Furthermore the reaction products may be isolated and recovered from the reaction using, as in the case of the reaction conditions themselves, procedures conventionally used in the art for conducting such reactions or analogous reactions.

The starting materials for reaction schemes A–E, above, may be prepared as follows:

An ester of o-toluic acid may be brominated to afford the corresponding benzyl bromide which may then be converted to the triphenylphosphonium bromide. This may then be condensed, in a Wittig reaction, with the appropriate metasubstituted (methyl, ethyl or n-propyl) benzaldehyde to afford a 3'-alkylstilbene-2-carboxylic acid, after hydrolysis of the ester function. This may then be hydrogenated and the product cyclized with, for example, polyphosphoric acid, to afford a 2-alkyl-10,11-dihydro-5H-dibenzo[a,d]cyclohepten-5-one. This compound may be converted to the 10,11-dehydro compound by bromination with, for example, N-bromosuccinimide, followed by dehydrobromination with, for example, diazabicyclononene in dimethylformamide. The benzylic position of the alkyl group may be brominated with, for example, N-bromosuccinimide, in carbon tetrachloride. The bromo compound may then be converted to the corresponding nitrile (II) by displacement with cyanide ion. Alternatively, the 5-oxo group may first be ketalized using a novel ketalization reaction involving reaction of the keto bromide with phosphorus pentachloride followed by the appropriate alcohol or glycol (e.g., ethylene glycol) and a tertiary amine such as triethylamine. This reaction is conveniently performed in an inert organic solvent such as benzene or acetonitrile, or mixtures thereof, at a temperature between about 0° and 50°C. This reaction is generally applicable to ketalization of compounds having, in place of bromo, other halo, nitrile, carboxy or carboxylic ester moieties.

The ketal bromide, prepared by the novel ketalization process, may then be converted to the ketal nitrile (IV) as described above. The ketal nitrile may be partially hydrolyzed, under basic conditions well known in the art, to afford the ketal amide (V) which may then, if desired, be deketalized under acid conditions generally used for removal of a ketal group, to afford the keto amide (III). Alternatively, the ketal nitrile may be completely hydrolyzed to afford the ketal acid, or a salt thereof (VI), under basic conditions well known for the hydrolysis of a nitrile group to an acid. Ketal esters (VI), may be prepared, for example, by acid catalyzed alcoholysis of a keto nitrile (II) or keto amide (III), followed by ketalization of the keto ester, as described above, using PCl$_5$ followed by an alcohol or glycol and a tertiary amine, or by esterification of the ketal acid (VI) with, for example, an alcohol such as methanol (on the acid chloride) or a diazoalkane such as diazomethane or diazoethane.

The ketals (VI) exhibit biological activity of the same type as free ketones (I), described supra.

The following examples illustrate preferred embodiments of the processes of the present invention. They should not be construed as limiting the scope or spirit of the invention in any manner. The yields of product obtained from the present process vary, depending upon the choice of starting materials, reagents, reaction condition, and workup. Generally, however, the yields are in the range of from 50 to about 95 percent.

PREPARATION 1

A. 118 Gm. of methyl o-toluate and 140 gm. of N-bromosuccinimide are refluxed, using a heat lamp, in 1.3 l. of carbon tetrachloride for one hour. The solution is cooled and filtered and the solvent removed under vacuum. The residual liquid is dissolved in 500 ml. of acetonitrile and 250 gm. of triphenylphosphine is added. The mixture is warmed then cooled and the o-carbomethoxybenzyltriphenylphosphonium bromide is filtered off (yield 271 gm., 69%).

116.5 Gm. of 1,5-diazobicyclo[3.4.0]nonene-5 is added to 107.5 gm. of m-tolualdehyde and 400 gm. of o-carbomethoxybenzyltriphenylphosphonium bromide in 2000 ml. of acetonitrile. The mixture is refluxed briefly then cooled and the solvent removed under vacuum. The residue is dissolved in chloroform and washed with dilute hydrochloric acid, and the solution dried and evaporated. The product is refluxed for 11 hours in a solution of 111 gm. potassium hydroxide in 1000 ml. of water and 150 ml. of methanol. The solution is cooled and extracted with chloroform. The aqueous solution is acidified with concentrated hydrochloric acid and extracted with chloroform. The extract is dried and evaporated to give 177.5 gm. (91%) of 3'-methylstilbene-2-carboxylic acid (ca. 60:40 cis:-trans). Use of m-ethylbenzaldehyde instead of m-tolualdehyde gives a similar yield of 3'-ethylstilbene-2-carboxylic acid.

B. A solution of 53.0 gm. of 3'-methylstilbene-2-carboxylic acid in 230 ml. dimethylformamide containing 2.0 gm. of 5% palladium on carbon is hydrogenated in a Parr shaker at 60 p.s.i. for 1½ hours. The solution is filtered and added to ether and water. The organic layer is washed with water, then dried and evaporated. The product is recrystallized from ether-hexane to give 48 gm., 90%, of 3-(o-carboxyphenethyl)toluene, m.p. 82°–84°C. Use of 3'-ethylenestilbene-2-carboxylic acid gives a similar yield of 3-(o-carboxyphenethyl)ethylbenzene.

C. 75 Gm. of 3-(o-carboxyphenethyl)toluene is dissolved in 400 ml. sulpholane and heated to 110°–120°C. 200 Ml. of polyphosphoric acid is added and the mixture is stirred at 100°C. for 90 minutes, and then poured onto ice and water. The mixture is extracted with hexane and the solution dried and evaporated to give 64 gm., 89%, of 2-methyl-10,11-dihydro-5H-dibenzo[a,d]cyclohepten-5-one as an oil. Use of 3-(o-carboxyphenethyl)ethylbenzene gives a similar yield of 2-ethyl-10,11-dihydro-5H-dibenzo [a,d]cyclohepten-5-one.

D. 60.5 Gm. of 2-methyl-10,11-dihydro-5H-dibenzo[a,d]cyclohepten-5-one is refluxed in 500 ml. of carbon tetrachloride with 58.2 gm. of N-bromosuccinimide for 8 hours. The solution is cooled and filtered and the solvent removed under vacuum. The residue is dissolved in 200 ml. of dimethylformamide and 44 gm. of 1,5-diazabicyclo[3.4.0]nonene-5 is added. The mixture is heated to 80°C. for 20 minutes, then cooled and added to water. The solution is extracted with ether and the extract washed, dried and evaporated. The residue is recrystallized from acetone/hexane to afford 39.7 g., 69% of 2-methyl-5H-dibenzo[a,d]cyclohepten-5-one, m.p. 78°–80°C. Use of 2-ethyl-10,11-dihydro-5H-dibenzo [a,d]cyclohepten-5-one gives a similar yield of 2-ethyl-5H-dibenzo[a,d]cyclohepten-5-one, m.p. 62°–64°C.

E. 39.7 Gm. of 2-methyl-5H-dibenzo[a,d]cyclohepten-5-one is refluxed in 1200 ml. of carbon tetrachloride with 35.2 gm. of N-bromosuccinimide for 14 hours, irradiating with a 100 watt incandescent lamp. The solution is cooled, filtered and evaporated. The residue is recrystallized from methylene chloride/hexane to afford 27.3 gm., 51%, of 2-bromomethyl-5H-dibenzo[a,d]cyclohepten-5-one, m.p. 128°–132°C. Use of 2-ethyl-5H-dibenzo[a,d]cyclohepten-5-one gives 80% of 2-(α-bromoethyl)-5H-dibenzo[a,d]cyclohepten-5-one, m.p. 93°–95°C.

F. 12.0 Gm. of sodium cyanide and 6.0 gm. of 2-bromomethyl-5H-dibenzo[a,d]cyclohepten-5-one are stirred at 100°C. for 40 minutes in 150 ml. of acetone cyanohydrin. The mixture is cooled and poured into ether. The ethereal layer is washed with water, dried and evaporated. The residue is chromatographed on 350 gm. of silica gel, eluting with hexane/ethyl acetate (3:2) to obtain 8.8 gm., 78%, of 5H-dibenzo[a,d]cyclohepten-5-on-2-yl acetonitrile which is recrystallized from ethyl acetate/hexane, m.p. 119°–121°C. Use of 2-(α-bromoethyl)-5H-dibenzo[a,d]cyclohepten-5-one gives a similar yield of 2-(5H-dibenzo[a,d]cyclohept-en-5-on-2-yl)propionitrile, m.p. 108°–109°C.

PREPARATION 2

A. 31.7 Gm. of 2-bromomethyl-5H-dibenzo[a,d]cyclohepten-5-one and 26.6 gm. of phosphorus pentachloride are stirred in 160 ml. of benzene until a clear solution is obtained. The solution is then added to a stirred, ice-cooled mixture of 72.9 ml. of ethylene glycol, 76 ml. of triethylamine and 380 ml. of acetonitrile. The mixture is warmed to room temperature and left for 1 hour, then poured into water. The solution is extracted with ether and the extract washed five times with water, then dried and evaporated to give 28.2 gm., 72%, of 5,5-ethylenedioxy-2-bromomethyl-5H-dibenzo[a,d]cycloheptene as a gum. NMR: $\delta^{CDCl_3}$ 4.45(s), 7.08(s), 7.87(d) ppm.

Use of 2-(α-bromoethyl)-5H-dibenzo[a,d]cyclohept-en-5-one produces a 92% yield of 5,5-ethylenedioxy-2-(α-bromoethyl)5H-dibenzo[a,d]cycloheptene as a gum. NMR: $\delta^{CDCl_3}$ 1.97(d), 5.17(g), 7.07(s), 7.86(d) ppm.

B. A solution of 26.9 gm. of 5,5-ethylenedioxy-2-bromo-methyl-5H-dibenzo[a,d]cycloheptene in 135 ml. of dimethylformamide is stirred at 25°C. for 24 hours with 4.62 gm. of sodium cyanide. The mixture is poured into water and extracted with ethyl acetate. The extract is washed with water, dried and evaporated to give 23.4, 90%, of 2-(5,5-ethylenedioxy-5H-dibenzo[a,d]cyclohepten-2-yl) acetonitrile as a gum. IR: $\nu_{max}^{CHCl_3 \, film}$ 2260 cm.$^{-1}$.

C. A solution of 122.4 gm. of 5,5-ethylenedioxy-2-(α-bromoethyl)5H-dibenzo[a,d]cycloheptene in 620 ml. of dimethylformamide is stirred at 50°C. for five hours with 20.6 g. of sodium cyanide. The solution is poured into water and extracted with ethyl acetate. The extract is washed with water, dried and evaporated to afford 102.6 gm., 98%, of 2-(5,5-ethylenedioxy-5H-dibenzo[a,d]cyclohepten-2-yl)propionitrile as a gum. NMR: $\delta^{CDCl_3}$ 1.55(d), 3.98(g), 7.07(s), 7.87(d) ppm.

PREPARATION 3

3.0 Gm. of 2-(5,5-ethylenedioxy-5H-dibenzo[a,d]cyclohepten-2-yl)propionitrile is refluxed for 3 hours in 50 ml. of water and 10 ml. of methanol containing 0.55 gm. of potassium hydroxide. The solution is cooled and extracted with ethyl acetate. The extract is washed with aqueous sodium carbonate and water, then dried and evaporated to yield 57% of 2-(5,5-ethylenedioxy-5H-dibenzo[a,d]cyclohepten-2-yl)propionamide. Use of 2-(5,5-ethylenedioxy-5H-dibenzo[a,d]cyclohepten-2-yl) acetonitrile and a one hour reaction time gives a similar yield of 2-(5,5-ethylenedioxy-5H-dibenzo[a,d-]cyclohepten-2-yl)acetamide.

PREPARATION 4

2.0 Gm. of 2-(5,5-ethylenedioxy-5H-dibenzo[a,d]cyclohepten-2-yl)propionamide is dissolved in 50 ml. of methanol and 5 ml. of N-hydrochloric acid is added. The mixture is heated to 50°C. for 30 minutes then cooled and added to water. The solution is extracted with ethyl acetate and the extract washed, dried and evaporated to yield 80% of 2-(5H-dibenzo[a,d]cyclohepten-5-on-2-yl)propionamide which is recrystallized from methanol, m.p. 158°–159°C. Use of 2-(5,5-ethylenedioxy-5H-dibenzo[a,d]cyclohepten-2-yl)acetamide gives a similar yield of 2-(5H-dibenzo[a,d]cyclohepten-5-on-2-yl)acetamide.

PREPARATION 5

0.7 Gm. of 2-(5,5-ethylenedioxy-5H-dibenzo[a,d]cyclohepten-2-yl)propionitrile is refluxed for 9 hours in 40 ml. of water containing 1.1 gm. of potassium hydroxide. The solution is cooled and neutralized with dilute hydrochloric acid, and extracted with ether. The ether extract is washed, dried and evaporated to afford a 75% yield of 2-(5,5-ethylenedioxy-5H-dibenzo[a,d]cyclohepten-2-yl)propionic acid. Use of 2-(5,5-ethylenedioxy)-5H-dibenzo[a,d]cyclohepten-2-yl)acetonitrile gives a similar yield of 2-(5,5-ethylenedioxy-5H-dibenzo[a,d]cyclohepten-2-yl)acetic acid.

PREPARATION 6

A. 1.0 G. of 2-(5H-dibenzo[a,d]cyclohepten-5-on-2-yl)propionic acid (preparation described infra) is dissolved in 25 ml. of chloroform, and 1 ml. of thionyl chloride and 0.1 ml. of dimethylformamide are added thereto. The mixture is left for 3 hours, then evaporated to dryness. The residue is dissolved in 20 ml. of benzene and evaporated to dryness. 0.5 G. of the residue is dissolved in 5 ml. of acetonitrile containing 1.0 ml. of methyl alcohol and 1.0 ml. of triethylamine. The mixture is left at room temperature for 16 hours, then poured into water. The solution is extracted with ether and the extract washed with water, dilute hydrochloric acid, aqueous sodium carbonate, dried and evaporated to yield the crude product which is dissolved in hexane-ether (1:1), the solution passed through silica gel, and the eluant evaporated to afford 2-(5H-dibenzo[a,d]cyclohepten-5-on-yl)propionic acid methyl ester in 80% yield as an oil which slowly crystallized, m.p. 37°–39°C. NMR: $\delta^{CDCl_3}$ 1.55(d), 3.67(s), 3.83(g), 7.04(s) ppm.

B. 5.0 G. of 2-(5H-dibenzo[a,d]cyclohepten-5-on-2-yl)propionic acid (preparation described infra) is suspended in 50 ml. of dioxane, added to excess ethereal diazomethane and stirred until dissolution is complete and evaporated to dryness. Purification as in part A on silica gel affords a nearly quantitative yield of 2-(5H-dibenzo[a,d]cyclohepten-5-on-2-yl)propionic acid methyl ester as in part A.

C. Use of 2-(5H-dibenzo[a,d]cyclohepten-5-on-2-yl)acetic acid in parts A and B gives similar yields of 2-(5H-dibenzo[a,d]cyclohepten-5-on-2-yl)acetic acid methyl ester, m.p. 67°–69°C.

PREPARATION 7

1.1 Gm. of 2-(5H-dibenzo[a,d]cyclohepten-5-on-2-yl)propionic acid methyl ester is stirred in 10 ml. of benzene containing 0.9 gm. of phosphorus pentachloride for one hour. The solution is then added to a stirred, ice cooled mixture of 2.4 ml. of ethylene glycol, 2.5 ml. of triethylamine, and 13 ml. of acetonitrile. The mixture is allowed to attain room temperature, and then water and ether are added. The ethereal layer is washed several times with water, then dried and evaporated to give a quantitative yield of 2-(5,5-ethylenedioxy-5H-dibenzo [a,d]cyclohepten-2-yl)propionic acid methyl ester. Use of 2-(5H-dibenzo[a,d]cyclohepten-5-on-2-yl)acetic acid methyl ester gives a similar yield of 2-(5,5-ethylenedioxy-5H-dibenzo[a,d]cyclohepten-2-yl)acetic acid methyl ester.

EXAMPLE 1

23.4 Gm. of 5,5-ethylenedioxy-5H-dibenzo[a,d]cyclohepten-2-yl acetonitrile is refluxed for seven hours in 160 ml. of acetic acid and 240 ml. of concentrated hydrochloric acid. The solution is cooled and added to ethyl acetate and water. The organic layer is washed with water then extracted with aqueous sodium carbonate. The extract is acidified with hydrochloric acid and extracted with ethyl acetate. The extract is dried and evaporated to afford the product which is recrystallized from acetone/hexane to give 9.5 gm., 50%, of 5H-dibenzo[a,d]cyclohepten-5-on-2-yl acetic acid, m.p. 148°–149.5°C. Use of 2-(5,5-ethylenedioxy-5H-dibenzo[a,d]cyclohepten-2-yl)propionitrile gives a 75% yield of 2-(5H-dibenzo[a,d]cyclohepten-5-on-2-yl)propionic acid, m.p. (chloroform-hexane) 138°–139°C.; m.p. (acetone-hexane) 113°–115°C.

EXAMPLE 2

A. 3.4 Gm. of 2-(5H-dibenzo[a,d]cyclohepten-5-on-2-yl)propionitrile is refluxed for 90 minutes in a mixture of 210 ml. of acetic acid and 300 ml. of concentrated hydrochloric acid. The mixture is cooled and ether and water are added. The organic layer is washed, dried and evaporated to give 3.4 gm., 93%, of 2-(5H-dibenzo[a,d]cyclohepten-5-on-2-yl)propionic acid, m.p. (chloroform-hexane) 138°–139°C.; m.p. (acetone-hexane) 113°–115°C. Use of 2-(5H-dibenzo[a,d]cyclohepten-5-on-2-yl)acetonitrile gives a similar yield of 2-(5H-dibenzo[a,d]cyclohepten-5-on-2-yl)acetic acid, m.p. (acetone-hexane) 148°–149.5°C.

B. The acids prepared in part A may also be prepared, via their salts, by basic hydrolysis using the procedure of Preparation 5.

C. 1.29 Gm. of 2-(5H-dibenzo[a,d]cyclohepten-5-on-2-yl)propionitrile and 0.85 gm. of p-toluenesulfonic acid monohydrate are refluxed for six hours in 25 ml. of methanol. The solution is cooled and added to water and ether. The ethereal solution is washed, dried and evaporated to give a 75% yield of 2-(5H-dibenzo[a,d]cyclohepten-5-on-2-yl)propionic acid methyl ester as an oil which slowly crystallized, m.p. 37°–39°C., NMR: $\delta^{CDCl_3}$ 1.55(d), 3.67(s), 3.83(g), 7.04(s) ppm. Use of 2-(5H-dibenzo[a,d]cyclohepten-5-on-2-yl)acetonitrile gives a similar yield of 2-(5H-dibenzo[a,d]cyclohepten-5-on-2-yl)acetic acid methyl ester, m.p. 67°–69°C.

EXAMPLE 3

A. 3.0 Gm. of 2-(5H-dibenzo[a,d]cyclohepten-5-on-2-yl)propionamide is refluxed in a mixture of 20 ml. of acetic acid and 30 ml. of concentrated hydrochloric acid for 3 hours. The solution is cooled and poured into water. The mixture is extracted with ethyl acetate and the extract is washed, dried and evaporated to yield 90% of 2-(5H-dibenzo[a,d]cyclohepten-5-on-2-yl)propionic acid., m.p. (chloroform-hexane) 138°–139°C.; m.p. (acetone-hexane) 113°–115°C. Use of 2-(5H- dibenzo[a,d]cyclohepten-5-on-2-yl)acetamide gives a similar yield of 2-(5H-dibenzo[a,d]cyclohepten-5-on-2-yl)acetic acid, m.p. (acetone-hexane) 148°–149.5°C.

B. The acids prepared in part A may also be prepared, via their salts, by basic hydrolysis using the procedure of Preparation 5.

EXAMPLE 4

11.0 Gm. of 2-(5,5-ethylenedioxy-5H-dibenzo[a,d]cyclohepten-2-yl)propionamide is refluxed for 2 hours in 70 ml. of acetic acid and 105 ml. of concentrated hydrochloric acid. The mixture is cooled and diluted, then extracted with ether. The ethereal solution is extracted with aqueous sodium carbonate and the extract acidified and extracted with ethyl acetate to afford a 70% yield of 2-(5H-dibenzo[a,d]cyclohepten-5-on-2-yl)propionic acid., m.p. (chloroform-hexane) 138°–139°C.; m.p. (acetone-hexane) 113°–115°C. Use of 2-(5,5-ethylenedioxy-5H-dibenzo[a,d]cyclohepten-2-yl)acetamide gives a similar yield of 2-(5H-dibenzo[a,d]cyclohepten-5-on-2-yl)acetic acid, m.p. (acetone-hexane) 148°–149.5°C.

EXAMPLE 5

2.0 Gm. of 2-(5,5-ethylenedioxy-5H-dibenzo[a,d]cyclohepten-2-yl)propionic acid is dissolved in 20 ml. of acetone and to the solution is added 20 ml. of N-hydrochloric acid. The mixture is refluxed for one hour, then cooled, diluted with water, and extracted with ethyl acetate. The extract is washed, dried, and evaporated to give a 90% yield of 2-(5H-dibenzo[a,d]cyclohepten-5-on-2-yl)propionic acid, m.p. (chloroform-hexane) 138°–139°C.; m.p. (acetone-hexane) 113°–115°C. Use of 2-(5,5-ethylenedioxy-5H-dibenzo[a,d]cyclohepten-2-yl)acetic acid gives a similar yield of 2-(5H-dibenzo[a,d]cyclohepten-5-on-2-yl)acetic acid, m.p. (acetone-hexane) 148°–149.5°C.

EXAMPLE 6

A. 2.0 Gm. of 2-(5,5-ethylenedioxy-5H-dibenzo[a,d]cyclohepten-2-yl)propionic acid methyl ester is stirred in 25 ml. of 1:1 concentrated sulfuric acid:water for 12 hours. The mixture is poured into water and extracted with ethyl acetate and the extract is washed, dried and evaporated to afford a 70% yield of 2-(5H-dibenzo[a,d]cyclohepten-5-on-2-yl)propionic acid, m.p. (chloroform-hexane) 138°–139°C.; m.p. (acetone-hexane) 113°–115°C. Use of 2-(5,5-ethylenedioxy-5H-dibenzo[a,d]cyclohepten-2-yl)acetic acid methyl ester gives a similar yield of 2-(5H-dibenzo[a,d]cyclohepten-5-on-2-yl)acetic acid, m.p. (acetone-hexane) 148°–149.5°C.

B. 1.0 Gm. of 2-(5,5-ethylenedioxy-5H-dibenzo[a,d]cyclohepten-2-yl)propionic acid methyl ester is dissolved in 10 ml. of acetone and to the solution is added 5 ml. of N-hydrochloric acid. The mixture is refluxed for one hour, then cooled, diluted with water, and extracted with ethyl acetate. The extract is washed with aqueous sodium carbonate and water, then dried and evaporated to afford a 75% yield of 2-(5H-dibenzo[a,d]cyclohepten-5-on-2-yl)propionic acid methyl ester, as an oil which slowly crystallized, m.p. 37°–39°C., NMR: $\delta^{CDCl_3}$ 1.55(d), 3.67(s), 3.83(g), 7.04(s) ppm. Use of 2-(5,5-ethylenedioxy-5H-dibenzo[a,d]cyclohepten-2-yl)acetic acid methyl ester gives a similar yield of 2-(5H-dibenzo[a,d]cyclohepten-5-on-2-yl)acetic acid methyl ester, m.p. 67°–69°C.

What is claimed is:

1. A compound represented by the formula

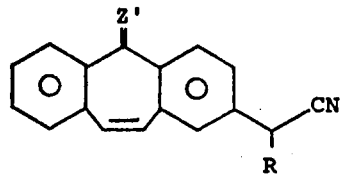

wherein R is hydrogen, methyl or ethyl and Z' is oxo.

2. The compound of claim 1 which is 2-(5H-dibenzo[a,d]cyclohepten-5-on-2-yl)acetonitrile.

3. The compound of claim 1 which is 2-(5H-dibenzo[a,d]cyclohepten-5-on-2-yl)propionitrile.

* * * * *